United States Patent [19]

Robert

[11] 4,097,603
[45] Jun. 27, 1978

[54] GASTRIC CYTOPROTECTION WITH NON-ANTISECRETORY DOSES OF PROSTAGLANDINS

[75] Inventor: André Robert, Kalamazoo, Mich.

[73] Assignee: The Upjohn Company, Kalamazoo, Mich.

[21] Appl. No.: 830,559

[22] Filed: Sep. 6, 1977

[51] Int. Cl.² .................. A61K 31/215; A61K 31/19
[52] U.S. Cl. ..................................... 424/305; 424/317
[58] Field of Search ............................ 424/305, 317

[56] References Cited

U.S. PATENT DOCUMENTS 3,953,495   4/1976   Hayashi et al. .................. 424/317

*Primary Examiner*—Sam Rosen
*Attorney, Agent, or Firm*—Robert A. Armitage

[57] ABSTRACT

The present invention provides a method for prophylaxis of certain gastric inflammatory diseases by administration of gastric cytoprotective prostaglandins. Gastric cytoprotective prostaglandins refer to those prostaglandin-type compounds which are useful in reducing or preventing development of ulcers and other gastric lesions in the rat challenged by ingestion of ethanol, but which exhibit substantially no gastric antisecretory effects at the effective dosage for the present method.

7 Claims, No Drawings

GASTRIC CYTOPROTECTION WITH NON-ANTISECRETORY DOSES OF PROSTAGLANDINS

BACKGROUND OF THE INVENTION

The present invention comprises the surprising and unexpected discovery that certain prostaglandin-type compounds represent gastric cytoprotective agents, useful in the prophylaxis of certain inflammatory diseases of the stomach and the duodenum.

Prostaglandins and prostaglandin analogs have previously been known in the treatment and prophylaxis of gastro-intestinal tract disorders. For example, the use of prostaglandin-type compounds in reducing gastric secretion, and thus treating or preventing gastric or duodenal ulcers is known in the art. See U.S. Pat. Nos. 3,903,297 and 3,781,429. Further, the concomitant use of prostaglandin-type compounds with a NOSAC (non-steroidal antiinflammatory compound, which is a prostaglandin synthetase inhibitor) is known to be effective to reduce the undesirable gastro-intestinal side effects of NOSAC administration. See U.S. Pat. Nos. 3,911,124; 3,917,828; 3,928,588; and 3,927,213. Further, the use of $PGE_2$ in preventing damage to the gastric mucosal barrier in the dog treated with a NOSAC such as aspirin or in domethacin is described by Cohen, M. M., in Gastroenterology 68:A-19/876 (1975).

Further, the prevention of gastric erosive diseases (e.g., gastric ulceration and erosive gastritis) with antacid or gastric acid antisecretory agents other than prostaglandins is likewise known in the art. See, for example, Mann, N. S., et al., Gastroenterology 68:A-88/945 (1975) which describes the use of metiamide (a gastric antisecretory agent) in preventing the gastric damage caused by the treatment of rats with aspirin and bile. See further, Mann, S., Gastroenterology 68:A-89/946 (1976) which describes the prevention of acute erosive gastritis by antacid administration.

This latter reference further describes the use of prostaglandin $E_2$ at doses of about 5–7 mg/kg per treatment in the prevention of bile-induced gastric erosions. For a discussion of the profound effect of $PGE_2$ in lowering gastric acid concentration in the rat at doses considerably lower than those reported by Mann, see Robert, A., et al., Gastroenterology 70:359 (1976). In particular, Robert describes a one-quarter to one-half reduction in gastric acid concentration as the dosage of prostaglandin $E_2$ is increased from 1 mg/kg to 2 mg/kg.

Further, prostaglandin $E_2$ has been employed in clinical studies as an agent to promote the healing of ulcers. See Karim, S. M. M., et al., "Some of the Naturally-Occurring Prostaglandins and Synthetic Analogs on Gastric Secretion and Ulcer Healing in Man," Advances in Prostaglandin and Thromboxane Research (Samuelson, B., et al., Eds.), Raven Press, New York (1976), pages 429–439, where a 1 mg. oral dose of prostaglandin $E_2$, provided every 6 hrs. for 2 weeks, is reported to yield a statistically significant increase in the percentage of ulcer healing as compared to untreated patients. The n-decyl ester of $PGE_2$ is also reported by Wada, Gastroenterologia Japonica, 9:155 (1974) to result in an improvement in the healing rate of ulcers at an oral dose of 6 mg/patient/day.

As indicated by Wada, cited above, the use of prostaglandins in the treatment of gastric ulcers can result in a significant incidence of side effects, such as diarrhea, when prolonged treatment with prostaglandin is employed.

The employment of enteric cytoprotective prostaglandins in the treatment and prevention of certain inflammatory intestinal diseases is described in U.S. Ser. Nos. 658,148 and 658,149, filed Feb. 17, 1976.

The prostaglandins refer to a family of cyclopentane containing carboxylic acids derived from mammalian tissues. Further, chemical analogs of these prostaglandins have been prepared and found to exhibit characteristic prostaglandin-like biological properties. See Bergstrom, et al., Pharmacological Review 20:1 (1968) for a discussion of the prostaglandins and characteristic biological properties thereof. For a discussion of representative analogs of the prostaglandins, see Ser. Nos. 658,148 and 658,149, referred to above.

SUMMARY OF THE INVENTION

The present invention provides a novel method for employing prostaglandin analogs in order to prevent gastric disease, principally gastritis and gastric or duodenal ulcers, by systemic administration of gastric cytoprotective prostaglandins.

In particular, the invention provides a method of preventing a non-NOSAC-induced gastric inflammatory disease in a human with high susceptibility to the acquisition of said disease, which comprises:

administering to said human systemically a non-antisecretory dose of a gastric cytoprotective prostaglandin effective to prevent the development of said disease.

More specifically the present invention provides a method of preventing gastric inflammatory disease in humans exhibiting (1) a history of multiple episodes of gastric or duodenal ulceration, (2) a history of chronic and excessive ethanol consumption, (3) a recent acute exposure to a cytodestructive dose of ionizing electromagnetic or particulate radiation, (4) an acute or chronic ingestive exposure to noxious gastric cytodestructive or gastric cytotoxic chemical agents, or (5) a recent exposure to pathogens capable of producing diseases characterized by untoward gastric symptoms, such as vomiting, which comprises:

administering systemically a non-antisecretory dose of a gastric cytoprotective prostaglandin effective to prevent the development of said disease.

With respect to the method described above, gastric inflammatory diseases include specifically gastric ulcer, duodenal ulcer and gastritis, although other gastric inflammatory conditions, such as those secondary to radiation exposure, are likewise included within its purview.

See U.S. Nos. 658,148 and 658,159 for a description of these sources of radiation for which the present invention provides cytoprotection.

A further aspect of the present invention resides in the selection of patients for the present method who exhibit a high susceptibility to the acquisition of gastric inflammatory diseases. In accordance with the invention, patients who will benefit from the gastric cytoprotective prostaglandin will fall into several classes. First, patients with a previous history of gastric or duodenal ulcer are known to be highly susceptible to a recurrence of this disease, and thus the present invention provides a method for preventing or reducing recidivism in such ulcer-prone patients. Moreover, those with two or more episodes of gastric ulcer, being particularly susceptible to the recurrence of gastric inflammatory disease, are especially contemplated as subjects for the chronic administration of the gastric cytoprotective prostaglandins of the present invention.

A further class of subjects which exhibit a high susceptibility to the acquisition of gastric inflammatory disease are those experiencing stressful environmental conditions, whether of physical or emotional origin. Such subjects particularly include those persons whose emotional disposition has been identified as a source of recurrent gastritis or a prior episode of gastric or duodenal ulcer disease.

Further, patients for whom treatment by the present method is indicated include persons exhibiting chronic and excessive ethanol consumption. In particular, the use of the present method by persons diagnosed as alcoholics, according to standard methods for the diagnosis of this disease, are contemplated by the present method. Especially suitable candidates for the present method are those alcoholics with a history of recurrent or persistent gastritis resulting from uncontrolled or uncontrollable consumption of ethanol.

Further included as suitable subjects for treatment by the present method are humans exhibiting acute exposure to cytodestructive doses of ionizing radiations. While ionizing radiation from any source is contemplated, particularly suitable subjects include patients exposed accidentally to high levels of radiation and those receiving measured doses of radiation for therapeutic reasons (e.g., in the treatment of neoplastic diseases). Cytodestructive doses of such radiation are those capable of producing the symptoms of gastric distress associated with radiation sickness.

Further included as suitable subjects for treatment by the present method are humans exhibiting acute or chronic ingestive exposure to noxious, gastric cytodestructive or gastric cytotoxic chemical agents. Particularly contemplated by the present invention are those persons who suffer an accidental, acute exposure to poisons or other agents which are noxious or erosive to the gastric tissues. For example, children who ingested ignested household chemicals, such as detergents, drain cleaners, and the like, are suitable subjects for treatment by the present method. in such an instance treatment is initiated following the usual emergency procedures, if any, which are indicated to control the systemic effects resulting from the ingested poison. Further included as suitable subjects for the present invention are those persons whose exposure to the noxious gastric cytodestructive or gastric cytotoxic chemical agents is of a more chronic nature. For example, those persons whose occupation requires them to formulate or apply economic poisons (e.g., pesticides and herbicides) likewise are subjects for the present invention. In particular, such persons who are chronically exposed to these chemical agents and such chronic exposure has resulted in at least a single episode of gastritis or gastric or duodenal ulcer resulting therefrom, are especially suitable for treatment in accordance with the present method. Further, humans exposed to therapeutic doses of chemotherapeutic agents used in the treatment of neoplastic diseases with known gastric cytotoxic or cytotoxic side effects provide further subjects for the present method.

Finally, the present invention is employed in subjects exhibiting a recent exposure to pathogens capable of producing diseases characterized by untoward gastric symptoms such as vomiting. Specifically contemplated by this application of the present invention are those persons who in travelling to foreign countries are likely to encounter or have encountered pathogens which have produced gastro-intestinal distress, and for whom a further exposure is contemplated.

The present invention requires administration of a non-antisecretory dose of the gastric cytoprotective prostaglandin effective to prevent the development of the gastric inflammatory disease. Thus, the dose required in accordance with the present invention is sufficiently great so as to permit the cytoprotective effect, but much smaller than those doses capable of producing any significant gastric antisecretory effect. For the purposes of the present invention, gastric cytoprotective prostaglandins are selected from among those prostaglandins or prostaglandin analogs which when orally administered to the rat are capable of completely inhibiting the formation of ethanol-induced gastric lesions in accordance with the following experimental procedure:

Female rats weighing 210–220 gm. are placed in cages capable of preventing coprophagy and the eating of hair. After fasting overnight, 1.0 ml. of 80% ethanol is administered orally. Test animals are treated with the gastric cytoprotective prostaglandin orally in 1.0 ml. of saline about 30 min. prior to the administration of ethanol, while control animals receive only saline vehicle. One hr. after ethanol injection, the animals are sacrificed by suffocation (carbon dioxide) and the stomach dissected out, being opened along the greater curvature, and examined for lesions or ulcers present in the corpus of the stomach (the glandular portion which secretes acid and pepsin). The incidence of ulcers is then recorded and the severity graded on a scale of 0–3 (from mild to most severe). An average numerical score is then determined on the basis of severity (mean severity) and the average number of ulcers per stomach determined. From these values the ulcer index is then calculated by adding (a) 10% of the percent incidence of animals with ulcers, (b) the mean severity of the ulcers present, and (c) the average number of ulcers per stomach. Accordingly, if all of the test animals exhibit ulceration (100% incidence) and a maximal mean severity of 3.0 were observed and the average number of ulcers per stomach were 20, the ulcer index for the test group would be 33 (10 + 3 + 20). Accordingly, 50% effective dose ($ED_{50}$) can be determined for any gastric cytoprotective prostaglandin based upon its ability to reduce the ulcer index by 50% as compared to the index obtained from control animals.

In accordance with the present invention a gastric cytoprotective prostaglandin is defined as any prostaglandin or prostaglandin analog which is active in the rat cytoprotective assay described above, but which exhibits an $ED_{50}$ as a gastric antisecretory agent, if any, in the rat which is at least 10 times and preferably 100 times greater than the $ED_{50}$ at which gastric cytoprotection is observed. For the purposes of determining an $ED_{50}$ for gastric secretion, experimental methods such as those described in Robert, et al., Gastroenterology 55:481 (1968) and 70:359 (1976), are conveniently employed.

Thus, the present gastric cytoprotective prostaglandins in accordance with the criteria described above are simply and efficiently determined by readily available procedures in a standard laboratory animal. Gastric cytoprotective prostaglandins thusly obtained include:
$PGE_1$;
$PGE_2$;
$PGA_1$;
$PGB_1$;
$PGF_2\alpha$;
$PGF_2\beta$;
$PGD_1$;
15-methyl-$PGF_2\beta$;
15-methyl-$PGF_1\beta$;
15-methyl-$PGF_2\beta$, methyl ester;
16,16-dimethyl-$PGE_2$;
15-methyl-$PGF_2\beta$, methyl ester;
15-methyl-$PGE_2$, methyl ester;
15-epi-15-methyl-$PGE_2$, methyl ester;
15-epi-15-methyl-$PGF_2\alpha$, methyl ester;
15-dehydro-$PGF_2\alpha$;
17-phenyl-18,19,20-trinor-$PGF_2\alpha$;
$PGA_2$, methyl ester;
15-epi-15-methyl-$PGF_2\alpha$, methyl ester;
cis-4,5-didehydro-$PGF_1\alpha$;
16,16-dimethyl-$PGA_2$;
15-methyl-$PGA_2$, methyl ester;
17-(p-chlorophenyl)-18,19,20-trinor-$PGE_2$, methyl ester, 15-methyl ether;
15-dehydro-$PGE_2$;
$8\beta,12\alpha$-$PGF_2\alpha$, methyl ester;
$8\beta,12\alpha$-$PGF_2\beta$, methyl ester;
2a, 2b-dihomo-17-phenyl-18,19,20-trinor-$PGE_2$, methyl ester, 15-methyl ether;
2a,2b-dihomo-17-phenyl-18,19,20-tetranor-$PGF_2\alpha$, methyl ester, 15-methyl ether.
15-epi-15-methyl-$PGF_2\alpha$, methyl ester;
$PGF_2\alpha$, 15-methyl ether;
15-methyl-$PGE_1$, methyl ester;
15-epi-15-methyl-11-deoxy-$PGF_1\alpha$, methyl ester;
15-epi-15-methyl-11-deoxy-$PGF_2\beta$, methyl ester;
16,16-dimethyl-$8\beta,12\alpha$-$PGE_2$, methyl ester;
11-deoxy-$PGE_1$, methyl ester, 15-methyl ether;
11-deoxy-$PGE_2$, methyl ester, 15-methyl ether;
11-deoxy-$PGF_1\beta$, methyl ester, 15-methyl ether;
15-epi-17-phenyl-18,19,20-trinor-$8\beta,12\alpha$-$PGE_2$, methyl ester;
9,11-dideoxy-$9\alpha,11\alpha$-epoxymethano-$PGF_1$, methyl ester;
15-epi-15-methyl-$PGF_2\alpha$, methyl ester;
$8\beta, 12\alpha$-$PGE_2$, methyl ester;
$PGD_2$;
5-oxa-$PGE_1$, methyl ester;
15-epi-5-oxa-$8\beta,12\alpha$-$PGA_1$;
$PGF_1\alpha$, methyl ester, 15-methyl ether;
$PGE_1$, methyl ester;
15-dehydro-cis-4,5-didehydro-$PGF_1\alpha$, methyl ester;
15-epi-15,16,16-trimethyl-$PGF_2\alpha$, methyl ester;
2a,2b-dihomo-$PGE_2$, methyl ester;
15-epi-16-phenoxy-17,18,19,20-tetranor-$8\beta,12\alpha$-$PGF_2\alpha$, methyl ester;
16-phenoxy-17,18,19,20-tetranor-$8\beta,12\alpha$-$PGF_2\beta$, methyl ester;
15-epi-15,16,16-trimethyl-$PGE_2$, methyl ester;
15-epi-15-methyl-$PGD_2$, methyl ester;
15-methyl-$PGD_2$, methyl ester;
$8\beta,12\alpha$-$PGE_2$;
9-deoxy-9,10-didehydro-15-methyl-$PGD_2$, methyl ester;
9-deoxy-9-hydroxymethyl-$PGF_2$;
cis-4,5-didehydro-$PGD_1$, methyl ester;
16,16-dimethyl-$PGA_2$, methyl ester;
$PGF_2\alpha$, 1,15-lactone;
$PGD_2$, methyl ester;
15-epi-2a,2b-dihomo-15-methyl-$PGF_2\alpha$, methyl ester;
2a,2b-dihomo-15-epi-15-methyl-$PGF_2\alpha$, methyl ester;
cis-4,5-didehydro-$PGE_1$;
cis-4,5-didehydro-$PGD_1$;
cis-4,5-didehydro-$PGA_1$;
2a,2b-dihomo-16,16-dimethyl-$PGF_2\alpha$;
2a,2b-dihomo-16,16-dimethyl-$PGF_1\alpha$, methyl ester;
9-deoxy-9,10-didehydro-$PGD_2$;
15-methyl-$PGF_2\beta$, methyl ester;
15-epi-15-methyl-$PGF_2\beta$;
16,16-dimethyl-cis-13-$PGE_2$;
15-epi-cis-4,5-didehydro-$PGF_1\alpha$;
15-epi-cis-4,5-didehydro-$PGF_1\beta$;
15-epi-cis-4,5-didehydro-$PGD_1$;
2,2-difluoro-15-methyl-$PGE_2$, methyl ester;
5-oxa-16,16-difluoro-$PGE_1$, methyl ester;
15-epi-15-methyl-$PGF_2\alpha$, 1,9-lactone;
16,16-difluoro-$PGE_2$;
cis-13-$PGE_1$;
15-epi-15-methyl-$PGF_2\beta$, 1,9-lactone;
5,6-didehydro-16,16-dimethyl-$PGE_2$;
13,14-didehydro-$PGF_1\beta$;
13,14-didehydro-$PGF_1\alpha$, 1,15-lactone;
$PGE_3$, methyl ester;
3,7-inter-m-phenylene-4,5,6-trinor-3-oxa-$PGE_1$;
17-(o-methoxyphenyl)-18,19,20-trinor-15-epi-$PGE_2$;
$8\beta,12\alpha$-13,14-didehydro-$PGF_2\alpha$;
13,14-didehydro-15-epi-$PGE_2$;
13,14-didehydro-15-epi-$PGE_1$;
9-deoxy-9-methylene-$PGF_2$;
13,14-didehydro-$PGF_1\alpha$, 1,9-lactone;
15-epi-15-methyl-9-deoxy-9-methylene-$PGF_2$;
15-methyl-9-deoxy-9-methylene-$PGF_2$;
15-epi-15-methyl-$PGE_1$;
13,14-didehydro-$8\beta,11\beta,12\alpha$-$PGE_1$;
15-epi-15-methyl-9-deoxy-9,10-didehydro-$PGD_2$;
16,16-dimethyl-$PGE_2$, p-benzamidophenyl ester;
$PGE_2$, ethyl amide; and
16,16-dimethyl-$PGF_2\alpha$.

As is readily apparent from the list described above, the instant gastric cytoprotective prostaglandins are effective as cytoprotective agents in accordance with the present invention regardless of whether or not they are capable of inhibiting gastric secretion at any dose.

Among the gastrocytoprotective prostaglandins those particularly preferred for the present purposes are those exhibiting little or no antisecretory activity at any dose. Accordingly, the preferred gastric cytoprotective prostaglandins are those where the ratio of the antisecretory $ED_{50}$ to the cytoprotective $ED_{50}$ in the rat is 100:1 or greater. Further preferred are those cytoprotective prostaglandins which are 100% effective ($ED_{100}$) in inhibiting gastric lesions in the rat at a dose less than or equal to 2 mg/kg, while exhibiting little or no uterotonic, luteolytic, or cardiovascular activity normally associated with the prostaglandins.

In the operation of the present invention any convenient systemic route of administration for the cytoprotective prostaglandin is employed. However, oral administration is the highly preferred route, although other routes such as via parenteral routes may be employed. See U.S. Pat. No. 3,903,297 for a description of the various methods of formulation for the prostaglandins as well as routes of administration encompassed by the present invention.

The dosage regimen and duration per treatment for the present cytoprotective prostaglandins will depend upon a wide variety of factors, including the type, age, weight, sex, and medical condition of the patient, and the nature and severity of the gastric inflammatory disease to be treated. Additionally, dosage will vary depending upon the particular cytoprotective prostaglandin to be administered, such dosages being, however, readily and efficiently determined from the relative potencies of these compounds in the rat gastric cytoprotective assay described above. A physician in possession of the patient's medical history or information relating to exposure to one of the conditions requiring treatment will readily determine the indication and duration for treatment and thus be capable of prescribing an effective amount of the gastric cytoprotective prostaglandin to prevent the development of the disease. For example, when antisecretory prostaglandin analogs are employed, the physician would by one method start at about 10% of the $ED_{50}$ of such a compound as an antisecretory agent and thereafter reduce the dosage to lower levels in accordance with the patient's response. For example, oral doses of between 25 mg/kg/day and 0.5 μg/kg/day will be adequate to insure the proper operation of the present invention. Once a minimum effective dose of a particular cytoprotective prostaglandin is determined for a particular patient, the patient is advantageously provided with a daily dosage schedule which will provide a substantially uniform level of cytoprotective prostaglandin throughout the day.

In any event the initial dosage selected should be non-antisecretory with respect to gastric acid. Thus, dosages, at which not more than a 10% reduction in gastric secretion is observed, are employed.

The treatment with the gastric cytoprotective prostaglandin should be continued so long as susceptibility to the gastric inflammatory disease remains high. Thus, in the case of acute exposure to a noxious agent, treatment for several days to several weeks will ordinarily be sufficient. In those cases where the patient has a history of recurrent gastric or duodenal ulcer, treatment may be maintained indefinitely, based on the patient's continued tolerance of the drug.

Accordingly, the present invention provides a novel and unexpected means of preventing ulcers by prostaglandin administration, without the need to affect the gastric secretory output. Thus, not only does the present invention provide surprising efficacy in that it can operate without altering acid secretion of the stomach, but it further employs such low doses of gastric cytoprotective prostaglandin that systemic side-effects are markedly diminished or not observed. Thus the prostaglandin or analog is better tolerated by the patient and represents a more appropriate and desirable therapeutic agent for prolonged administration than the antisecretory prostaglandins previously known in the prevention of gastric inflammatory disease.

I claim:

1. A method of preventing non-NOSAC-induced gastric inflammatory disease in a human with high susceptibility to the acquisition of said disease, which comprises:
administering to said humans systemically a non-antisecretory dose of a gastric cytoprotective prostaglandin effective to prevent the development of said disease.

2. A method of preventing gastric inflammatory disease in a human exhibiting:
(1) a history of multiple episodes of gastric or duodenal ulceration,
(2) a history of chronic and excessive ethanol consumption;
(3) a recent acute exposure to a cytodestructive dose of ionizing electromagnetic or particulate radiation;
(4) an acute or chronic ingestive exposure to noxious, gastric cytodestructive or gastric cytotoxic chemical agents,
or
(5) a recent exposure to pathogens capable of producing diseases characterized by untoward gastric symptoms such as vomiting,
which comprises:
administering systemically a non-antisecretory dose of a gastric cytoprotective prostaglandin effective to prevent the development of said disease.

3. A method according to claim 2, wherein said human exhibits a history of multiple episodes of gastric or duodenal ulceration.

4. A method according to claim 2, wherein said human exhibits a history of chronic and excessive ethanol consumption.

5. A method according to claim 2, wherein said human exhibits a recent acute exposure to a cytodestructive dose of ionizing electromagnetic or particulate radiation.

6. A method according to claim 2, wherein said human exhibits an acute or chronic ingestive exposure to noxious gastric cytodestructive or gastric cytotoxic chemical agents.

7. A method according to claim 2, wherein said human exhibits a recent exposure to pathogens capable of producing diseases characterized by untoward gastric symptoms.

* * * * *

UNITED STATES PATENT OFFICE
CERTIFICATE OF CORRECTION

Patent No. 4,097,603         Dated June 27, 1978

Inventor(s) Andre Robert

It is certified that error appears in the above-identified patent and that said Letters Patent are hereby corrected as shown below:

Column 2, line 58, "U.S. Nos. 658,148 and 658,159" should read -- U.S. Serial Nos. 658,148 and 658,149 --;

Column 6, line 4, "$PGF_2\alpha$," should read -- $PGF_2\beta$, --; line 42, "$PGF_2\alpha$" should read -- $PGF_2\beta$ --.

Signed and Sealed this

Tenth Day of July 1979

[SEAL]

*Attest:*

*Attesting Officer*

LUTRELLE F. PARKER
*Acting Commissioner of Patents and Trademarks*